(12) United States Patent
Feiweier et al.

(10) Patent No.: US 10,012,714 B2
(45) Date of Patent: Jul. 3, 2018

(54) METHOD AND DEVICE FOR OPTIMIZING MAGNETIC RESONANCE SYSTEM OPERATING SEQUENCES WITH RESPECT TO PHYSIOLOGICAL LIMITING VALUES

(71) Applicant: Siemens Aktiengesellschaft, Munich (DE)

(72) Inventors: Thorsten Feiweier, Poxdorf (DE); Peter Speier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 519 days.

(21) Appl. No.: 14/680,334

(22) Filed: Apr. 7, 2015

(65) Prior Publication Data
US 2015/0285885 A1      Oct. 8, 2015

(30) Foreign Application Priority Data

Apr. 7, 2014   (DE) .................. 10 2014 206 636

(51) Int. Cl.
| | |
|---|---|
| *G01V 3/00* | (2006.01) |
| *G01R 33/54* | (2006.01) |
| *G01R 33/36* | (2006.01) |
| *G01R 33/28* | (2006.01) |
| *A61B 1/00* | (2006.01) |

(52) U.S. Cl.
CPC ......... *G01R 33/543* (2013.01); *G01R 33/288* (2013.01); *G01R 33/36* (2013.01); *A61B 1/00* (2013.01); *A61B 2218/00* (2013.01); *G06F 2101/00* (2013.01)

(58) Field of Classification Search
CPC ......... A61B 1/00; A61B 2218/00; G06F 1/00; G06F 2101/00; G06T 1/00; G06T 2200/00

See application file for complete search history.

(56) References Cited

U.S. PATENT DOCUMENTS

| | | | |
|---|---|---|---|
| 8,954,202 B2 | 2/2015 | Feiweier | |
| 9,632,160 B2* | 4/2017 | Grodzki | ............... G01R 33/543 |
| 2007/0085537 A1* | 4/2007 | Feiweier | ............... G01R 33/246 |
| | | | 324/307 |

(Continued)

OTHER PUBLICATIONS

Feiweier et al: "Verfahrung zur Ansteuerung der Gradienten bei der MR-Bildgebung, unter Berücksichtung der durch Gradientensystem and Stimulationen vorgegebenen Limitierungen", Siemens Technik Report, vol. 5, No. 16, (2002).

*Primary Examiner* — Jermele M Hollington
*Assistant Examiner* — Temilade Rhodes-Vivour
(74) *Attorney, Agent, or Firm* — Schiff Hardin LLP

(57) ABSTRACT

A method and device for establishing a protocol relating to a measurement sequence for controlling a magnetic resonance tomography system, the measurement sequence is segmented into various groups of partial modules that are similar to one another. A partial module that potentially generates the greatest physiological exposure for a patient is identified. Furthermore, a test is carried out by means of a model function to determine whether physiological limiting values are being observed in the measurement sequence for the partial module. If the physiological limiting values are not being observed, parameters influencing the measurement sequence are modified and the preceding test step is repeated.

22 Claims, 3 Drawing Sheets

(56) References Cited

U.S. PATENT DOCUMENTS

| | | | |
|---|---|---|---|
| 2011/0234228 A1* | 9/2011 | Block | A61B 5/055 324/314 |
| 2012/0229136 A1* | 9/2012 | Stemmer | G01R 33/56383 324/307 |
| 2013/0033262 A1* | 2/2013 | Porter | A61B 5/055 324/309 |
| 2013/0063144 A1* | 3/2013 | Feiweier | G01R 33/56341 324/309 |
| 2014/0278195 A1 | 9/2014 | Feiweier et al. | |

* cited by examiner

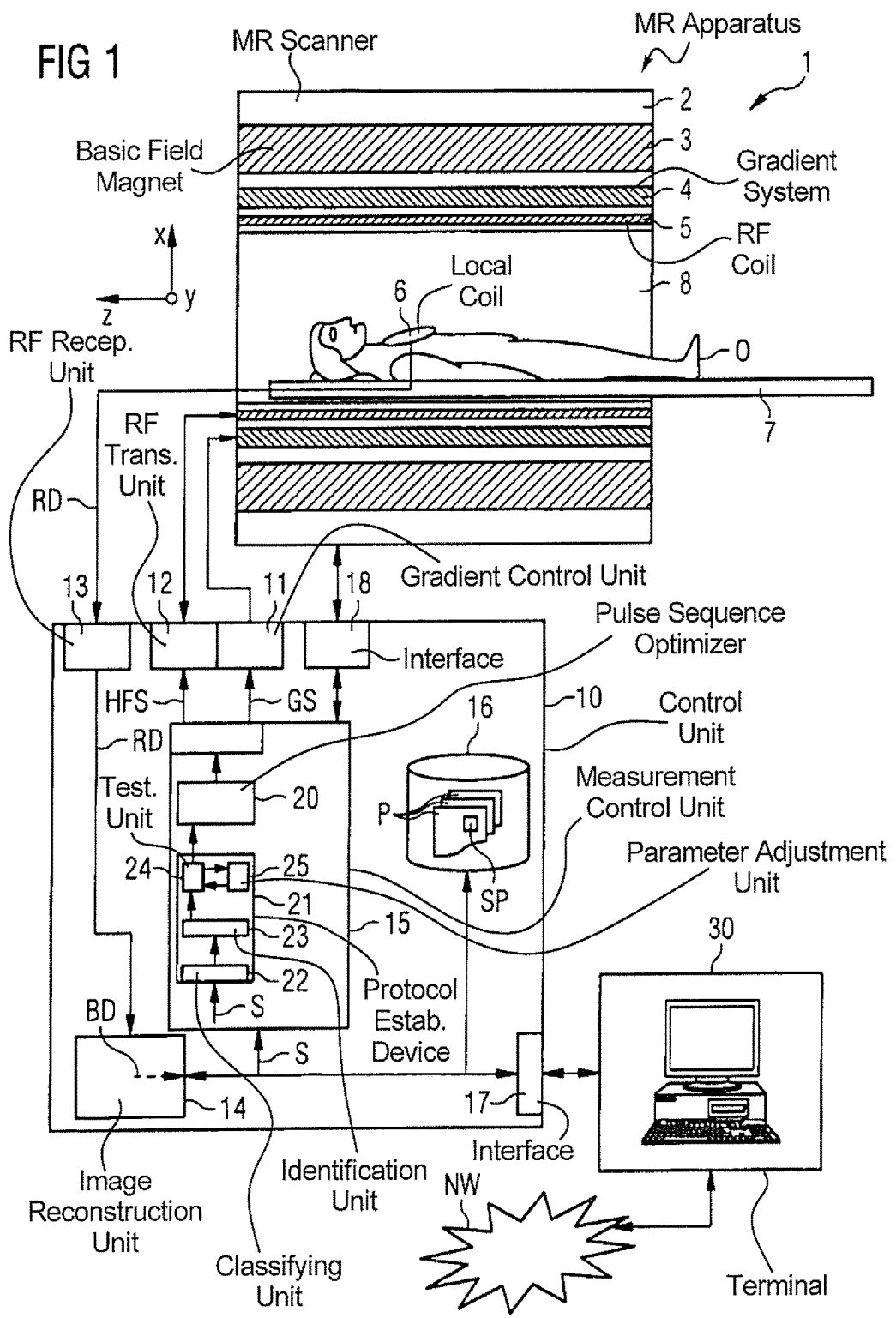

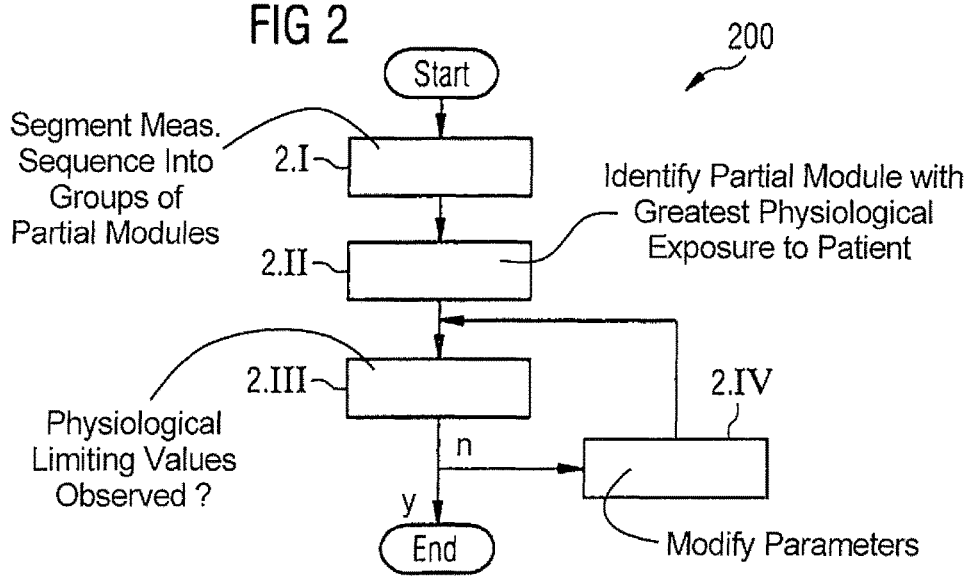
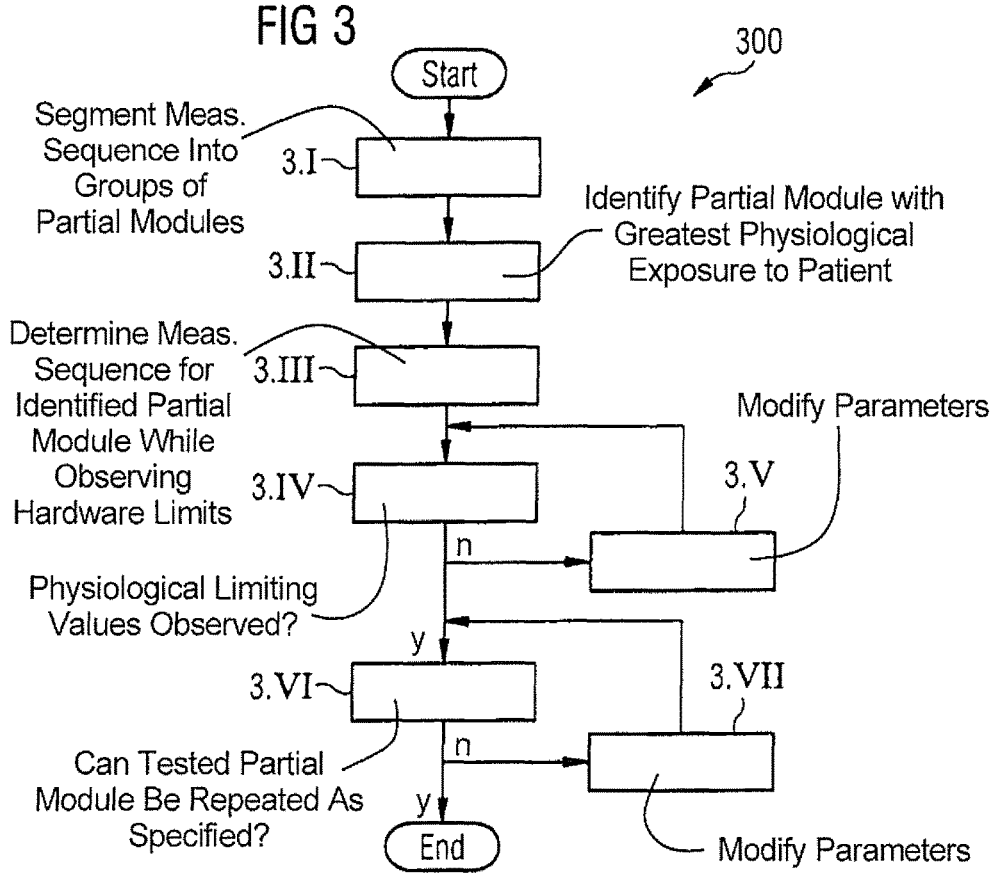

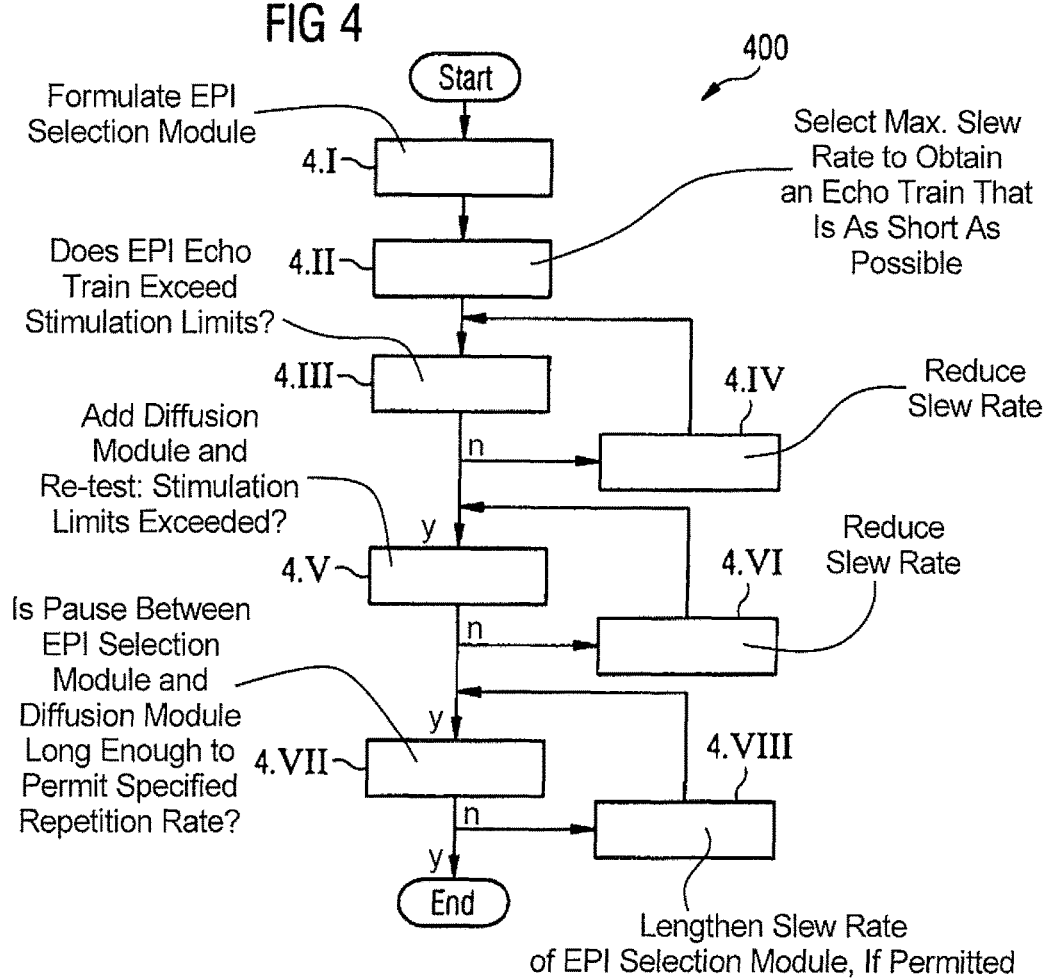
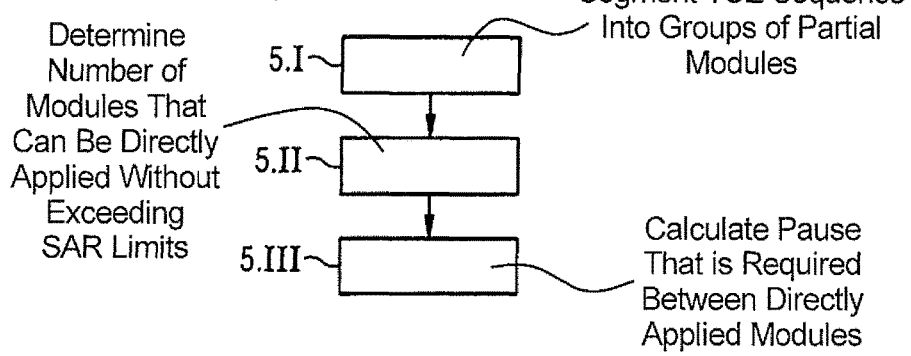

METHOD AND DEVICE FOR OPTIMIZING MAGNETIC RESONANCE SYSTEM OPERATING SEQUENCES WITH RESPECT TO PHYSIOLOGICAL LIMITING VALUES

BACKGROUND OF THE INVENTION

Field of the Invention

The invention relates to a method for establishing an optimized protocol relating to a measurement sequence for operating a magnetic resonance tomography system, and to a device for establishing an optimized protocol relating to a measurement sequence for operating a magnetic resonance tomography system.

The invention further relates to a magnetic resonance apparatus having a radio-frequency (RF) transmission system, with a gradient system and a control computer, which is designed to control the radio-frequency transmission system and the gradient system in order to carry out a desired measurement on the basis of such an optimized protocol.

Description of the Prior Art

In a magnetic resonance apparatus, also known as a magnetic resonance tomography system, the body that is to be examined is usually exposed to a relatively high basic magnetic field of for example 1, 3, 5 or 7 Tesla produced by a basic field magnet. In addition, a magnetic field gradient is applied by a gradient system. Radio-frequency excitation signals (RF signals) are then transmitted via a radio-frequency transmission system using appropriate antenna devices, so as to cause nuclear spins of certain atoms that have been resonantly excited by this radio-frequency field to be tilted by a defined flip angle with respect to the magnetic field lines of the basic magnetic field. During the relaxation of the nuclear spins, radio-frequency signals known as magnetic resonance signals are emitted. These signals are received by appropriate receiving antennas, and then further processed. The desired image data can finally be reconstructed from the raw data acquired in this way.

A specific pulse sequence thus must be transmitted for a specific measurement (data acquisition), this sequence being composed of a succession of radio-frequency pulses, in particular excitation pulses and refocusing pulses, and gradient pulses that are to be transmitted appropriately coordinated therewith in various spatial directions. Appropriately-timed selection windows have to be set that specify the timeframes in which the magnetic resonance signals that have been induced are acquired. Of significance for the imaging is the timing within the sequence, that is, which pulses succeed one another at which time intervals. A number of control parameters are usually defined in a combination known as a measurement protocol that is established in advance and that can be retrieved from a memory, for example, for a specific measurement, and optionally modified on-site by an operator who can specify additional control parameters, such as, for example, a specific slice distance in a stack of slices to be measured, and/or a slice thickness, etc. All these parameters are then used to calculate a pulse sequence, which is also referred to as a measurement sequence.

The gradient pulses can be defined, for example, by their gradient amplitude, their gradient pulse duration and, in the case of trapezoidal gradient pulses, by the edge steepness or the first derivative dG/dt of the pulse shape of the gradient pulses, also known as the "slew rate" or rate of increase S. A further key gradient pulse value is the gradient pulse moment (also known for short as the "moment"), which is defined by the integral of the gradient amplitude over time.

With the increasing capability of MR scanners, it is often the case that physiological limits set the boundary for the feasibility of certain measurement sequences. Thus, for example, the maximum capability of the gradient system (described using the maximum slew rate S and the maximum amplitude G) may not be exploited in certain measurement sequences (for example in a rapid succession of gradient pulses with a high amplitude and alternately signed, as in echo-planar imaging), because limiting values for peripheral nerve stimulation would otherwise exceeded. A similar problem arises in the utilization of the capability of the RF transmission system (described by the maximum and the mean transmission output). Measurement sequences with a rapid sequence of energy-intensive RF pulses are limited by legally-imposed values for energy absorption (SAR).

In the prior art, physiological limits are taken into account only relatively late in the measurement sequence. During the preparation of the measurement protocol (for example, setting the size of the matrix, the FOV (Field of View), the number and position of the slices, the contrast parameters etc.), physiological limits are ignored and only simple technical limits are taken into account. The latter can ensue either in a very abstract form by appropriate mean values or using hardware model functions (see, for example, DE 10 2008 015261 B4). It is only directly before the start of the measurement that a test is carried out to determine whether physiological limits are being exceeded. In the event that exceeding of a limit is detected, the user can switch to a measurement protocol that complies with physiological limits but he/she has a very limited selection of modifications to protocol parameters to choose from. For example, the FOV can be enlarged or, in a measurement that involves slice selection, the slice thickness can be increased or a reference gradient slew rate can be reduced (the latter having repercussions on the Time to Echo TE, for example).

One reason for the fact that the physiological aspects are dealt with at a later stage can be attributed to the relatively high level of computation involved. To estimate the stimulation potential, it is necessary, for example, to identify those segments of the measurement from which the highest values are anticipated. The details of the gradient applications are calculated (the measurement sequence is "rolled out"), and with the use of model assumptions (according to the SAFE model, for example, cf. DE 199 135 47 A1), a test is carried out to ensure that limiting values are being observed.

With respect to the SAR aspect, the fact that this is considered at a later stage may also be necessary because the energy input is not yet known at the time when the protocol is prepared. It may be the case, for example, that relevant results from adjustment measurements that determine the RF energy required to achieve a specific rotation angle or flip angle of the precessing spins are not yet available at the time when a measurement protocol is set, because the measurements have not yet been carried out.

It is also sometimes the case in the prior art that conservative assumptions are simply made when calculating the measurement sequence. This involves, for example, artificially limiting the gradient slew rates for certain parts of the measurement sequence "on suspicion" in order to reduce the stimulation potential for this part of the measurement. In many cases, however, the limit will turn out to be too conservative, which restricts the bandwidth of possible measurement protocols.

DE 10 2008 015 261 B4 describes an operating method for a computer for determining optimized control sequences for a medical imaging unit. The computer determines a group of temporary control sequences for power control devices in the unit such that the power control devices are in a position to control image-influencing emission devices pertaining to the unit that are controlled by the emission devices according to the temporary control sequences that have been determined and that the control of the emission devices according to the temporary control sequences of the respective group, insofar as it relates to the control of the emission devices, corresponds with the measurement sequence that is to be carried out. Furthermore, exposure curves are determined for the respective groups of control sequences.

In most applications, taking RF stimulation into account at a late stage through a modal dialog is considered to be so disruptive that, regardless of the protocol, the sequence parameters are restricted to such an extent that the stimulation threshold is exceeded only in rare exceptional cases. In this context, modal dialog means that the dialog has to be answered and thus completed in order to continue the investigation.

"Siemens Technik Report" Vol. 5, No. 16, April 2002, page 40ff, describes a method with which spiral trajectories can be optimized, taking into account physiological limits. It relates to a highly specific application based on the determination of trajectories by means of differential equations. Wider application of this approach to key imaging methods used in clinical practice is not possible. The method described in the "Siemens Technik Report" is very much customized for the spiral trajectory: starting from an analytical description (using differential equations), it then moves on to a numerical description (via differential equations), in which a check is carried out in each calculation step to see whether stimulation limits have been exceeded and a trajectory parameter (the maximum slew rate, for example) is then adapted where necessary for the next steps. In particular, this approach cannot be used to estimate the stimulation potential over a plurality of repetitions: if two spiral trajectories are to be completed in succession, the second would, for historical reasons, have to start with lower slew rates—hence the trajectories would no longer be identical.

SUMMARY OF THE INVENTION

An object of the present invention is to provide a more effective and more user-friendly method of establishing a protocol for a measurement sequence.

In the method according to the invention for establishing a protocol for a sequence of measurements to control a magnetic resonance tomography system, the sequence of measurements, that is, the pulse sequence that is to be transmitted to the MR scanner during the measurement, is segmented into different groups of partial modules that are similar to one another, and a partial module that potentially generates the greatest physiological exposure for a patient is subsequently identified. A test is then carried out using a model function to determine whether physiological limiting values are being observed in the measurement sequence for the partial module. Pre-established models for the method used for the observation of patient safety requirements can be employed as model functions. For peripheral nerve stimulation, for example, the SAFE model or even simpler models based on time-related changes in the magnetic fields (dB/dt) can be used. For energy deposition, direct use can be made, for example, of the standards from INC 60601-2-33 or also of more complex heat flow rate models. If the testing shows that the physiological limiting values are not being observed, the parameters that influence the measurement sequence are modified and the previous test step is subsequently repeated. The influencing parameters can include, for example, the gradient slew rate, the Time to Echo and the Time of Repetition. The partial modules can include, for example, a pulse sequence segment having the length of a Time of Repetition TR of gradient echo or spin echo imaging or be set by acquiring a slice by echo-planar imaging. Partial modules that are similar to one another means pulse sequence segments of the same or of a similar function type. In echo-planar diffusion imaging, for example, the central partial module in the echo-planar diffusion imaging is segmented into the following function groups: diffusion-encoding module, EPI selection module and pause. The diffusion-encoding module or EPI selection modules can be seen as different types of partial modules, partial modules of the same type being identical or at least similar to one another.

The method according to the invention takes physiological limits into account during the preparation of the protocol itself and to authorize only protocols that comply with the physiological limits. First, this simplifies the working procedure because no subsequent protocol modifications need to be carried out which have to be understood, evaluated and acknowledged. Second, the sequencing procedure with the method can be adjusted to the limits very much more flexibly, which, depending on the practical application, allows shorter Times to Echo, for example, and hence a better signal-to-noise ratio SNR and/or shorter Times of Repetition TR and hence a shorter measurement time.

Compared with the conventional approaches described above, the method according to the invention makes abstractions at a somewhat higher level (the modules) and considers relationships between a number of modules. This results, for example, in minimum distances being necessary in order to repeat identical modules as often as desired. The method according to the invention can furthermore be integrated seamlessly into existing sequence architectures or software architectures on a modular basis, that is, no completely new architecture concepts need to be introduced.

The device according to the invention for establishing a protocol for a sequence of measurements to control a magnetic resonance tomography system has a classification unit, which is designed to segment the measurement sequence into different groups of partial modules that are similar to one another. The device further has an identification unit, which is designed to identify a partial module that will potentially generate the greatest physiological exposure for a patient. The device further has a testing unit, which is designed to test by means of the model function whether physiological limiting values are being observed. Finally, the device also includes a parameter adjustment unit, which is designed to modify the influencing parameters and forward the modified parameters to the testing unit for fresh testing if the physiological limiting values are not being observed.

The magnetic resonance apparatus according to the invention includes the device according to the invention.

The invention also includes a non-transitory, computer-readable data storage medium that can be loaded directly into a memory of the device according to the invention, encoded with program code segments in order to carry out all the steps in the method according to the invention when running in the device according to the invention. Such a software-based design has the advantage that existing control devices of magnetic resonance units can be modified by implementing the program in an appropriate manner in order to set a measurement protocol in a manner according to the invention.

In an embodiment of the invention, the measurement sequence for the partial module is determined such that hardware limits are observed.

In a further embodiment, the step involving the determination of the measurement sequence for the partial module such that hardware limits are observed is carried out before testing whether physiological limiting values are being observed in the measurement sequence for the partial module.

In an alternative embodiment, if the physiological limiting values are being observed, a check is carried out to determine whether the partial module with the predetermined repetition rate can be repeated at least as often as has been specified without exceeding physiological limits. In addition, if a result of the test in the previous step is negative, the repetition rate is reduced and/or the partial module is further modified by modifying the influencing parameters and repeating the test step.

According to a variant of the method, the repetition rate is reduced by setting pauses between individual partial modules.

For example, the length of the pauses can be selected as a function of physiological limiting values.

The method according to the invention can be carried out such that the determination of the measurement sequence for the partial module such that hardware limits are observed and the test to determine whether physiological limiting values are being observed in the measurement sequence are carried out together. Consequently, a standardized model relating to hardware limits and the physiological limits can be used for testing whether limiting values are being observed, taking into account at least two parameters to be tested regarding the exceeding of limiting values, at least one relating to the hardware and at least one relating to the physiological aspects.

In the step that involves identification of a partial module that will potentially generate the greatest physiological exposure for a patient, a number of partial modules can alternatively also be identified.

Furthermore, a change in the slice orientation of the measurement protocol can additionally be taken into account in the test to determine whether physiological limiting values are being observed.

The test to determine whether physiological limiting values and/or hardware limits are being observed can already take place during the preparation of the measurement protocol or during the implementation of a patient-unrelated protocol planning by the user and/or by an automatic program, by the test being incorporated into the calculation of the permitted parameter zones and protocol parameters that would lead to the exceeding of the physiological limiting values and/or hardware limits being restricted accordingly. The method can be used not only to adjust the protocol to the patient ("online" editing), but also for patient-unrelated protocol planning ("offline" editing) if the limiting values used are known and are patient-unrelated (conservative estimates, for example). The protocol preparation does not necessarily have to be carried out directly by the user, but can also be performed in part by a program, using predefined scripts, for example. This can be used in particular in order to simplify patient-specific parameter changes that can only be carried out during an investigation.

The physiological limiting values can include stimulation with gradient fields and/or exposure to radio-frequency fields (SAR).

The influencing parameters can include, for example, the gradient slew rate, the Time to Echo and the Time of Repetition.

BRIEF DESCRIPTION OF THE DRAWINGS

FIG. 1 schematically illustrates a magnetic resonance apparatus according to an exemplary embodiment of the invention.

FIG. 2 is a flowchart that illustrates a method according to a first exemplary embodiment of the invention.

FIG. 3 is a flowchart that illustrates a method according to a second exemplary embodiment of the invention.

FIG. 4 is a flowchart that illustrates a method according to a third exemplary embodiment of the invention.

FIG. 5 is a flowchart that illustrates a method according to a fourth exemplary embodiment of the invention,

DESCRIPTION OF THE PREFERRED EMBODIMENTS

FIG. 1 shows a block diagram of a magnetic resonance MR apparatus 1 designed according to the invention. It includes, first, the actual magnetic resonance scanner 2 with an examination receptacle or patient tunnel 8 located therein. A bed 7 can be slid into the patient tunnel 8, such that a patient O or test subject lying thereon can be disposed during an investigation in a specific position inside the magnetic resonance scanner 2 relative to the magnet system and radio-frequency system arranged therein, or can be moved between various positions during a measurement.

Basic components of the magnetic resonance scanner 2 are a basic field magnet 3, a gradient system 4 with magnetic field gradient coils to generate magnetic field gradients in the x-, y- and z-directions, in addition to a whole-body radio-frequency (RF) coil 5. The magnetic field gradient coils in the x-, y- and z-directions can be controlled independently of one another such that, through a predetermined combination, gradients can be applied in any spatial directions (for example, in the slice selection direction, in the phase encoding direction or in the selection direction), these directions generally being dependent on the slice orientation that has been selected. The spatial directions can likewise also coincide with the x-, y- and z-directions, for example, the slice selection direction in the z-direction, the phase encoding direction in the y-direction and the selection direction in the x-direction. The reception of the magnetic resonance signals induced in the investigation subject O can be achieved via the whole body coil 5, with which the radio-frequency signals used to induce the magnetic resonance signals are usually also transmitted. Usually, however, these signals are received, for example, by a local coil arrangement 6 using, for example, local coils arranged on or under the patient O. All these components are basically known to those skilled in the art and are therefore only shown in schematic form in FIG. 1.

The components of the magnetic resonance scanner 2 can be controlled by a control device 10. The control device 10 can be a control computer that can be formed by multiple individual computers—optionally spatially separated and connected to one another by suitable cables or links. A terminal interface 17 connects this control device 10 to a terminal 30, via which an operator can control the entire unit 1. In the present case, this terminal 30 is configured as a computer with a keyboard, one or a number of screens, and also further input devices, such as, for example, a mouse or suchlike, so that a graphic user interface is made available to the operator.

The control device 10 has, among other things, a gradient control unit 11, which again can include multiple subcomponents. The individual gradient coils are switched on by control signals according to a gradient pulse sequence. As described in the aforementioned, these are gradient pulses that are set (run) during a measurement at precisely predetermined chronological positions and with a precisely predetermined time schedule.

The control device 10 additionally has a radio-frequency transmission unit 12 in order to supply the respective radio-frequency pulses, according to a predetermined radio-frequency pulse sequence RFS of the pulse sequence MS, to the radio-frequency whole-body coil 5. The radio-frequency pulse sequence RFS includes the aforementioned excitation- and refocusing pulses. The reception of the magnetic resonance signals is achieved with the use of the local coil arrangement 6, and the raw data RD received thereby are selected and processed by an RF reception unit 13. The magnetic resonance signals are forwarded in digital form as raw data RD to a reconstruction unit 14, which reconstructs the image data BD therefrom and stores these data in a memory 16 and/or forwards them via the interface 17 to the terminal 30, so that the operator can review them. The image data BD can also be stored and/or displayed and evaluated at other locations via a network NW. Alternatively, a radio-frequency pulse sequence can also be transmitted via the local coil arrangement and/or the magnetic resonance signals can be received by the whole-body radio-frequency coil (not shown), depending on the present connection status of the whole-body radio-frequency coil 5 and of the coil arrangements 6 to the radio-frequency transmission unit 12 or RF receiving unit 13.

Via a further interface 18, control commands are transmitted to further components of the magnetic resonance scanner 2, such as the couch 7, for example, or the basic field magnet 3, or measured values or other data are received.

The gradient control unit 11, the RF transmission unit 12 and the RF receiving unit 13 are coordinated in each case by a measurement control unit 15. Using corresponding commands, this unit ensures that the desired gradient pulse sequences GS and radio-frequency pulse sequences RFS are transmitted. In addition, it has to be ensured that the magnetic resonance signals on the local coils in the local coil arrangement 6 are selected and further processed by the RF receiving unit 13 at the appropriate time. The measurement control unit 15 likewise controls the interface 18. The measurement control unit 15 can for example, be formed by a processor or multiple processors. It is then possible to implement a pulse sequence-optimizer 20, in the form of appropriate software components, for example, with which facility an additional optimization of pulse sequence segments or pulse sequences can be carried out on the basis of a set, optionally already optimized protocol.

The basic sequence for such a magnetic resonance measurement and the aforementioned components for the control thereof (apart from the device 21 for establishing a protocol to control a magnetic resonance tomography system that has been specifically designed in the present case) are known to those skilled in the art, so they need not be further discussed in detail herein. Moreover, such a magnetic resonance scanner 2 and also the control device pertaining thereto may also include further components, which likewise are not explained in detail herein. At this stage, it is pointed out that the magnetic resonance scanner 2 can also be constructed in a different manner, for example, with a patient chamber that is open at the side, or as a smaller scanner, in which only one part of the body can be positioned.

In order to start a measurement, via the terminal 30, an operator can usually select a control protocol P provided for this measurement from a memory 16, in which a number of control protocols P for various measurements are stored. This control protocol P contains among other things various control parameters SP for the respective measurement. These control parameters SP include certain basic specifications for the desired pulse sequence, for example, the sequence type, that is, whether it is a spin echo sequence, a turbo-spin echo sequence etc. They further include control parameters regarding the magnetization strengths to be achieved with the individual radio-frequency pulses, specifications regarding the k-space gradient trajectory to be followed for the acquisition of raw data and furthermore, slice thicknesses, slice distances, number of slices, resolution, Times of Repetition, the Times to Echo in a spin echo sequence, etc.

With the aid of the terminal 30, the operator can change some of these control parameters in order to establish an individual control protocol for a measurement desired at the current time. For this purpose, modifiable control parameters are provided in order to make a change, for example, on a graphic user interface 30.

Moreover, the operator can also access control protocols from a manufacturer of the magnetic resonance system, for example, via a network NW and then optionally modify and use them.

On the basis of the control parameters SP, a pulse sequence S or measurement sequence is determined, with which the actual control of the remaining components ultimately ensues via the measurement control unit 15. The pulse sequence S can be calculated or configured in a pulse sequence-determination facility, which can be implemented for example, in the form of software components on a computer of the terminal 30. The pulse sequence-determination facility can also be part of the control device 10 itself, in particular of the measurement control unit 15. The pulse sequence-determination facility could likewise be implemented in a separate computation system, which for example, is connected to the magnetic resonance unit via the network NW.

When setting the control parameters, limiting values relating to the resilience of the hardware and also the physiological resilience of patients must be taken into account in particular. For this purpose, provision is made according to the invention for a device 21 for establishing a protocol to control a magnetic resonance tomography system, which device is used to adapt the protocols to the limiting values. The device 21 can be part of the control device 10. It can also be implemented as software on the terminal 30.

For example, FIG. 1 illustrates the device 21 for establishing a protocol to control a magnetic resonance tomography system as part of the control device 10. The device 21 has a classifying unit 22, which is equipped to segment the measurement sequence into a series of similar partial modules. To be more precise, the measurement sequence is segmented into different groups of partial modules that in each case are similar to one another. The device 21 further has an identification unit 23, which is designed to identify a partial module that will potentially generate the greatest physiological exposure for a patient. The device 21 further has a testing unit 24, which is designed to test, by means of the model function, whether physiological limiting values are being observed. The device 21 in FIG. 1 also has a parameter adjustment unit 25, which is designed to modify the influencing parameters and forward the modified parameters to the testing unit for a new test if the physiological limiting values are not being observed. The device 21 can also further have an additional testing unit, which is designed to test the measurement sequence with respect to hardware limits. The function that involves testing the hardware limits can also be carried out by the same testing unit that tests the physiological limits. The two tests can also be carried out in a process step that is coordinated for both limits. If the physiological limiting values for individual partial modules are observed, the testing unit can additionally check whether the partial module with the predetermined repetition rate can be repeated at least as often as specified without exceeding physiological limits. The testing unit 24 can also be designed to test whole sequences of partial modules for the observation of physiological limits such as hardware limits. The adjustment unit 25 can also be designed to reduce the repetition rate and/or further modify the partial module by changing the influencing parameters if the test result is negative in this case. The repetition rate can be reduced, for example, by setting pauses between individual partial modules.

FIG. 2 illustrates a method according to a first exemplary embodiment. In step 2.I, the measurement sequence is first segmented into various groups of partial modules that are similar to one another. In step 2.II, a partial module is identified that will potentially generate the greatest physiological exposure for a patient. In step 2.III, a test is carried out by means of a model function to check whether physiological limiting values are being observed in the measurement sequence for the partial modules. If the physiological limiting values are being observed, which is characterized in FIG. 2 by "y", the method is terminated. If the physiological limiting values are not being observed, which is characterized in FIG. 2 by "n", the influencing parameters for the measurement sequence are modified in step 2.IV and the previous testing step, that is, step 2.III, is repeated. The influencing parameters can be, for example, the gradient slew rate, the Time to Echo and the Time of Repetition.

The model functions to be used for the method are already specified by the methods used to comply with patient safety requirements. The SAFE model can be used for peripheral nerve stimulation, for example, or even simpler models based on time-related changes in the magnetic fields (dB/dt). For energy deposition, direct use can be made, for example, of the standards from IFC 60601-2-33 or also of more complex models of heat flow rate.

FIG. 3 shows a flowchart that illustrates a method according to a second exemplary embodiment of the invention. In step 3.I, the measurement sequence is segmented into different groups of partial modules that are similar to one another. For example, a partial module can include a pulse sequence segment with the length of a Time of Repetition TR of gradient echo or spin echo imaging or can be set by acquiring a slice by means of echo-planar imaging. In step 3.II, the partial module that potentially generates the greatest physiological exposure for a patient is identified. For example, the greatest physiological exposure may occur during the acquisition of the outer k-space lines, that is, when the strongest phase-encoding gradients are applied. In a step 3.III, the measurement sequence of the partial module is determined such that hardware limits are observed. This is initially carried out without taking physiological limits into account. In step 3.IV, a test is carried out using a model function(s) to determine whether the physiological limiting values are being observed. If the physiological limiting values are being observed, which is marked in FIG. 2 with "y", the method continues with a step 3.VI. If the physiological limiting values are not being observed, the influencing parameters are modified in a step 3.V. For example, the gradient slew rate is reduced. Step 3.IV is subsequently repeated. If the physiological limiting values are being observed, which is marked in FIG. 2 with "y", the method continues with a step 3.VI. In step 3.VI, a test is carried out to check whether the partial module that has been tested can be repeated at least as often as specified, without exceeding physiological limits. If that is the case, which is marked in FIG. 2 with "y", the method is terminated. If the physiological limits are being exceeded, which is marked in FIG. 2 with "n", the repetition rate can be reduced in step 3.VII. This can ensue, for example, by the insertion and/or extension of a pause. Furthermore, the partial module can be further modified by modifying the influencing parameter that relates to low physiological exposure rates. Step 3.VI can subsequently be repeated.

The stepwise approach in steps 3.III and 3.IV is possible since a reduction of the physiological exposure does not lead to an acceleration of the sequence but typically leads to a lengthening of the partial modules, which also reduces the stress on the hardware. Steps 3.III and 3.IV can alternatively also be carried out together depending on the respective implementation thereof. Insofar as the exceeding of physiological limits depends on specified parameters (for example, on the result of adjustment measurements), then these parameters can already be determined before starting to prepare the protocol. For example, the relevant adjustment measurements can already be determined for the respective couch position when moving the patient in on the couch, and can be stored such that they can be accessed as required. Alternatively, the parameters required can be determined using heuristic assumptions—optionally dependent on the patient's registration data, such as height, weight, age, sex, position etc. This procedure is advisable in particular for SAR limits. In some circumstances, the partial module with the greatest stimulation cannot be determined ad hoc in step 3.II. This may be the case, for example, if two phase-encoding gradients are used at the same time in the 3D imaging and—as with elliptical scanning—the two gradients do not reach their respective maximum at the same time. In this case, steps 3.III to 3.V can also be carried out repeatedly with different partial modules. Insofar as physiological limits directly depend on the positioning of the patient, this can be directly taken into account. This is important, for example, with peripheral nerve stimulations, in which the stimulation potential of a gradient pulse depends on the position of the axis thereof relative to the patient. The modification of the slice orientation of the measurement protocol by the user, could thus, for example, lead to limits being exceeded, and the measurement sequence could automatically carry out corresponding modifications to the sequence. Alternatively the measurement sequence could from the onset plan the measurement sequence such that the physiological limits for any slice orientations are observed by, for example, one or more of prospective "maximum exposure" orientations being tested. In this case, the measurement protocol would therefore be set such that the physiological and/or hardware-specific limiting values would be observed in any case, irrespective of which slice orientation is selected for the measurement.

Testing whether limits have been exceeded can already be carried out by the user during the preparation of the protocol. If the testing is integrated into the permitted parameter zones ("binary search"), protocol parameters that would lead to the exceeding of limits are restricted accordingly, by the framework that already exists, for example. The framework that already exists is understood to mean the architecture implemented hitherto or currently or a possible architecture of sequence and user interface. In the context of current architecture, "green", "red" and "grey" value zones are displayed for each measurement parameter. The user can select a value in the "green zone" without adjustments of other parameters being necessary. When a value in the "red" zone is selected, the system is aware of solution strategies, which lead to a valid, that is, to a practicable measurement protocol, with automatic adjustment of other parameters. Values in the "grey" zone are not practicable and are therefore not selectable. Through the integration of the method according to the invention into this architecture, the user can directly see which parameters he/she actually has to set, also taking into account physiological limits, or see which further parameter modifications have to be carried out automatically if the "red" zones are selected. Existing strategies in the conventional sequence schedule for solving parameter conflicts (for example, "TE can be reduced if TR is increased at the same time") can continue to be used in an adapted form. Since many (magnitude: 30-100) parameter variations have to be tested within a time that is negligible for the user (for example, <300 ms) in order to calculate the permitted zones, the testing of a parameter setting cannot take longer than about 2 ms.

If longer checking times are necessary, the framework has to be extended in order to carry out the check once again for the new parameters after calculating the permitted zones. In this case, it is not until after the input of the new value that the user knows whether the protocol observes or exceeds the limits. In the event of the limits being exceeded, either a user dialog with correction proposals can be displayed or predefined strategies can be carried out automatically with or without the user being notified. This method is advisable if the checking and calculation of the proposals is possible within about 200 ms.

If only the checking, but not the calculation of the proposals is possible within 200 ms, the calculation can be started manually by the user so as not to interrupt the interactive protocol preparation. As a planning aid, information on the exposure level is supplied to the user by a UI (user interface) element in the form of a quantitative display, (the stimulation as a percentage of the maximum permitted stimulation, for example, which is similar to the current SAR display) or in the form of a warning light. If the display shows that a limiting value has been exceeded, then the user can either reverse the parameter modifications ("undo" on the menu), reduce the exposure again by an appropriate parameter modification, or start the proposed calculation manually, for example by clicking with the mouse on the display.

Through the segmentation of the measurement into partial modules, the volume of computation required to evaluate whether physiological limits have been exceeded is kept within boundaries. Furthermore, the computing capacity available at the present time allows the necessary computation steps to be completed at a sufficiently fast rate (that is, during the preparation of the protocol by the user). Of course, in step 3.III the limits of the hardware do not have to be fully exploited—it is still possible for at least some functional sub-modules to be configured with conservative settings in order to thus reduce the frequency with which step 3.IV has to be carried out. In order to thus reduce the complexity in the calculation of a measurement sequence that complies with physiological limits, a certain safety margin from the actual limiting value can be provided in the evaluation of the model function(s). For example, the limiting values are only exploited to 90%—in this way, smaller contributions from the measurement sequence (for example, RF pulses having a low energy dose or gradient pulses with a low amplitude) can initially be ignored in the calculations, without these contributions later leading to limits being exceeded.

FIGS. 4 and 5 show two specific examples in which the method according to the invention can be used. The exemplary embodiment shown in FIG. 4 is directed at echo-planar diffusion imaging EPI (EPI=echo planar imaging). The central partial module in the echo-planar diffusion imaging consists of the following function groups: diffusion-encoding module, EPI selection module and pause. In the diffusion-encoding module few (for example, 2-4) gradient pulses with high amplitude are applied. In the EPI selection module on the other hand, a greater number (for example, 32-256) of gradient pulses with alternating polarity and moderate amplitude are applied in a very short time sequence. Initially, for example, in a step 4.I only the EPI selection module is considered. In the simplest case, the amplitude of the gradient pulses is calculated directly from the protocol parameters such as the FOV and the matrix size. In step 4.II (which corresponds to 3.II and 3.III), the maximum gradient slew rate is selected in order to obtain an echo train that is as short as possible (and hence a low level of image distortions). Then, in step 4.III (which corresponds to step 3.IV), a check is carried out with the aid of the model function to determine whether the EPI selection train exceeds stimulation limits. If these limits are being exceeded, which is marked in FIG. 4 with "n", the gradient slew rate is reduced in step 4.IV (which corresponds to step 3.V) and there is a return to step 4.III. Finally, the gradient rate is progressively reduced (and implicitly the inter-echo-spacing is increased) until the limits are observed, which is marked in FIG. 4 with "y". In step 4.V (which corresponds to step 3.I and step 3.II), the diffusion-encoding module is added. A test is now carried out again with the aid of the model function to determine whether the successive sequence of diffusion-encoding module+EPI selection module leads to stimulation limits being exceeded, that is, the stimulation limits are not being observed (which corresponds to step 3.IV). If the stimulation limits are not being observed, which is marked in FIG. 4 with "n", the gradient slew rates for the diffusion module can be reduced in a step 4.VI (and implicitly the Time to Echo TE can be increased). Then there is a return to step 4.V. Finally, the gradient rates are progressively reduced until the limits are observed, which is marked in FIG. 4 with "y" (which corresponds to step 3.V). If the stimulation limits are being observed, a test is carried out in a step 4.VII, again with the aid of model functions, to determine whether the pause set between a sequence of diffusion modules and EPI selection modules is sufficiently long to repeat the sequence of diffusion modules and EPI selection modules as often as planned in the measurement protocol, taking the stimulation limits into account (which step corresponds to step 3.VI). If this is not the case, which is marked in FIG. 4 with "n", the pause is optionally extended in duration accordingly in a step 4.VIII (which corresponds to step 3.VII). Subsequently there is a return to step 4.VII. Now if the stimulation limits are being observed, which is marked in FIG. 4 with "y", the method is successfully terminated. Depending on the practical application, in step 4.VIII, if the diffusion—and the EPI selection module are considered simultaneously, the gradient slew rate of the EPI selection module can also be lengthened, if observation of the limits can still be achieved therewith. Depending on the situation and the user's requirements, it is thus possible to achieve either as short as possible a selection train (few distortions) or as short as possible a Time to Echo (high SNR=high signal-to-noise ratio) or as short as possible a pause (short measurement time).

The exemplary embodiment illustrated in FIG. 5 takes into account SAR-related limits. In this application, the time constants in the model are generally longer. Thus, according to TEC 60601-2-33, in the exemplary embodiment illustrated in FIG. 4, a higher mean energy input into the body can ensue over a period of 10 seconds than in the embodiment illustrated in FIG. 5 over a period of 6 minutes. A TSE sequence that is frequently limited with regard to SAR, in particular at higher field strengths, encompasses the function modules: excitation, selection train, and pause. A corresponding segmentation into partial modules can be carried out in a step 5.I. The duration of such a partial module ranges from a few milliseconds up to several hundred milliseconds. By means of the model function(s), it is now possible to determine, in a step 5.II for example, the number N of such partial modules that can be applied directly one after another without exceeding short-term SAR limits. Furthermore, in a step 5.III, it is possible to calculate the type of pause that must be provided after N partial modules in order to observe long-term SAR limits. The measurement can thus be carried out in a corresponding "burst" mode with short "activity" phases (N partial modules), interrupted by moderate pauses. Advantageously, such a burst mode can be aligned, for example, with respiratory gating or with the breath-holding technique: the intrinsic measurement pauses are thus used at the same time to observe physiological limits, and in the activity phases it is possible to work nevertheless with a maximum measurement output.

According to the method described, physiological limits are taken into account when setting an optimized measurement sequence. The limits are already tested here during the precalculation of the sequence of measurement events (gradient pulses or RF pulses, for example) and, if necessary, adjustments are made. The volume of calculations involved can be minimized by using prior knowledge about the exposure generated by individual parts of the sequence and by using prior knowledge about the course of the sequence.

It is noted that the features of all the exemplary embodiments or of further developments disclosed in the figures can be used in any combination.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for establishing a protocol for a measurement sequence for operating a magnetic resonance tomography system comprising:
    providing a measurement sequence to a computer and, in said computer automatically segmenting said measurement sequence into a plurality of different groups of partial modules, with all partial modules in each different group performing a similar function in said measurement sequence;
    in said computer, identifying a partial module that produces a greatest physiology altering exposure to patient;
    in said computer testing said identified partial module with respect to a modeled function of the function performed by the identified partial module, to determine whether physiological limiting values, which limit an amount of said physiology altering, are observed by said measurement sequence for the identified partial module;
    in said computer, if said testing determines that said physiological limiting values are not being observed in said measurement sequence, modifying parameters that influence said measurement at least once in order to obtain modified parameters that cause said physiological limiting value to be observed by said measurement sequence for the partial module with the modified parameters; and
    in said computer, generating an operating protocol from said measurement parameters with said modified parameters for said identified partial module, and making said protocol available in electronic form at an output of said computer in a form for operating said magnetic resonance tomography system.

2. A method as claimed in claim 1 comprising, in said computer, determining parameters for the identified partial module that cause said measurement sequence to observe hardware limits of said magnetic resonance tomography system.

3. A method as claimed in claim 2 comprising determining said parameters for said partial module that cause said measurement sequence to observe said hardware limits before said testing.

4. A method as claimed in claim 2 comprising, in said computer, determining together whether said hardware limits are observed and testing whether said physiological limiting values are observed.

5. A method as claimed in claim 1 comprising:
    if said testing determines that said physiological limiting values are observed by the measurement sequence with the identified partial module, determining whether said partial module can be repeated at a specified repetition rate while still causing said physiological limiting values to be observed; and
    if said partial module cannot be repeated at said specified repetition rate without still observing the physiological limiting values, repeating said testing after performing at least one of reducing said repetition rate and further modifying said parameters of said partial module in order to obtain modified parameters that cause said physiological limiting value still to be observed.

6. A method as claimed in claim 5 comprising reducing said repetition rate by introducing pauses between respective partial modules of said measurement sequence.

7. A method as claimed in claim 6 comprising selecting a duration of said pauses as a function of said physiological limiting values.

8. A method as claimed in claim 1 comprising identifying and testing multiple partial modules that exhibit said greatest physiological exposure for said patient.

9. A method as claimed in claim 1 wherein said protocol designates a slice orientation from which magnetic resonance data are to be obtained by operating said magnetic resonance tomography system, and using said slice orientation in said testing as to whether said physiological limiting values are observed.

10. A method as claimed in claim 1 comprising employing, as said physiological limiting values, at least one of stimulation by gradient fields and exposure to radio-frequency fields.

11. A method as claimed in claim 1 wherein said parameters that are modified are selected from the group consisting of gradient slew rate, time to echo, and repetition time.

12. A method as claimed in claim 1 wherein each of said partial modules of said measurement sequence comprises radiation of a radio-frequency (RF) pulse having an associated RF energy, and wherein said physiology altering exposure is a specific absorption rate (SAR) of the patient.

13. A method as claimed in claim 1 wherein each of said partial modules of said measurement sequence comprises activation of a gradient pulse, and wherein said physiology altering exposure is peripheral nerve stimulation caused by said gradient pulse.

14. A device to establish a protocol to operate a magnetic resonance tomography system, said device comprising:
a computer having an input interface that receives a measurement sequence;
said computer being configured to automatically segment said measurement sequence into a plurality of different groups of partial modules, with all partial modules in each different group performing a similar function in said measurement sequence;
said computer being configured to identify a partial module that produces a greatest physiology altering exposure to patient;
said computer being configured to test said identified partial module with respect to a modeled function of the function performed by the identified partial module, to determine whether physiological limiting values, which limit an amount of said physiology altering, are observed by said measurement sequence for the identified partial module;
said computer being configured, if said testing determines that said physiological limiting values are not being observed in said measurement sequence, to modify parameters that influence said measurement at least once in order to obtain modified parameters that cause said physiological limiting value to be observed by said measurement sequence for the partial module with the modified parameters;
an output interface; and
said computer being configured to generate an operating protocol from said measurement parameters with said modified parameters for said identified partial module, and to make said protocol available in electronic form at said output interface of said computer in a form for operating said magnetic resonance tomography system.

15. A device as claimed in claim 14 wherein each of said partial modules of said measurement sequence comprises radiation of a radio-frequency (RF) pulse having an associated RF energy, and wherein said physiology altering exposure is a specific absorption rate (SAR) of the patient.

16. A device as claimed in claim 14 wherein each of said partial modules of said measurement sequence comprises activation of a gradient pulse, and wherein said physiology altering exposure is peripheral nerve stimulation caused by said gradient pulse.

17. A magnetic resonance apparatus comprising:
a computer having an input interface that receives a measurement sequence;
said computer being configured to automatically segment said measurement sequence into a plurality of different groups of partial modules, with all partial modules in each different group performing a similar function in said measurement sequence;
said computer being configured to identify a partial module that produces a greatest physiology altering exposure to patient;
said computer being configured to test said identified partial module with respect to a modeled function of the function performed by the identified partial module, to determine whether physiological limiting values, which limit an amount of said physiology altering, are observed by said measurement sequence for the identified partial module;
said computer being configured, if said testing determines that said physiological limiting values are not being observed in said measurement sequence, to modify parameters that influence said measurement at least once in order to obtain modified parameters that cause said physiological limiting value to be observed by said measurement sequence for the partial module with the modified parameters;
an output interface; and
said computer being configured to generate an operating protocol from said measurement parameters with said modified parameters for said identified partial module, and to make said protocol available in electronic form at said output interface of said computer in a form for operating said magnetic resonance scanner.

18. A magnetic resonance apparatus as claimed in claim 17 wherein each of said partial modules of said measurement sequence comprises radiation of a radio-frequency (RF) pulse having an associated RF energy, and wherein said physiology altering exposure is a specific absorption rate (SAR) of the patient.

19. A magnetic resonance apparatus as claimed in claim 17 wherein each of said partial modules of said measurement sequence comprises activation of a gradient pulse, and wherein said physiology altering exposure is peripheral nerve stimulation caused by said gradient pulse.

20. A non-transitory, computer-readable data storage medium encoded With programming instructions, said storage medium being loaded into a control computer of a magnetic resonance tomography system, and said programming instructions causing said control computer to:
receive a measurement sequence to a computer and automatically segment said measurement sequence into a plurality of different groups of partial modules, with all partial modules in each different group performing a similar function in said measurement sequence;
identify a partial module that produces a greatest physiology altering exposure to patient;
test said identified partial module with respect to a modeled function of the function performed by the identified partial module, to determine whether physiological limiting values, which limit an amount of said physiology altering, are observed by said measurement sequence for the identified partial module;
if said testing determines that said physiological limiting values are not being observed in said measurement sequence, modify parameters that influence said measurement at least once in order to obtain modified parameters that cause said physiological limiting value to be observed by said measurement sequence for the partial module with the modified parameters; and
generate an operating protocol from said measurement parameters with said modified parameters for said identified partial module, and make said protocol available in electronic form at an output of said computer in a form for operating said magnetic resonance tomography system.

21. A storage medium as claimed in claim 20 wherein each of said partial modules of said measurement sequence comprises radiation of a radio-frequency (RF) pulse having an associated RF energy, and wherein said physiology altering exposure is a specific absorption rate (SAR) of the patient.

22. A storage medium as claimed in claim 20 wherein each of said partial modules of said measurement sequence comprises activation of a gradient pulse, and wherein said physiology altering exposure is peripheral nerve stimulation caused by said gradient pulse.

\* \* \* \* \*